(12) United States Patent
Ruan et al.

(10) Patent No.: US 12,221,470 B2
(45) Date of Patent: Feb. 11, 2025

(54) YEAST-FERMENTED RECOMBINANT FIBRONECTIN PEPTIDE IN SMALL MOLECULE, AND ITS PREPARATION METHOD AND APPLICATIONS THEREOF

(71) Applicant: MELLGEN (SHENZHEN) BIOTECHNOLOGY CO., LTD., Guangdong (CN)

(72) Inventors: Renquan Ruan, Guangdong (CN); Longping Wen, Guangdong (CN)

(73) Assignee: MELLGEN (SHENZHEN) BIOTECHNOLOGY CO., LTD., Shenzhen (CN)

( * ) Notice: Subject to any disclaimer, the term of this patent is extended or adjusted under 35 U.S.C. 154(b) by 665 days.

(21) Appl. No.: 17/606,699

(22) PCT Filed: Feb. 24, 2020

(86) PCT No.: PCT/CN2020/076337
§ 371 (c)(1),
(2) Date: Oct. 26, 2021

(87) PCT Pub. No.: WO2020/228390
PCT Pub. Date: Nov. 19, 2020

(65) Prior Publication Data
US 2022/0220190 A1     Jul. 14, 2022

(30) Foreign Application Priority Data

May 10, 2019 (CN) .......................... 201910388775.3

(51) Int. Cl.
| | |
|---|---|
| A61K 8/64 | (2006.01) |
| A61K 9/00 | (2006.01) |
| A61K 38/39 | (2006.01) |
| A61K 38/46 | (2006.01) |
| A61Q 19/00 | (2006.01) |
| C07K 14/39 | (2006.01) |
| C07K 14/78 | (2006.01) |
| C07K 19/00 | (2006.01) |
| C12N 9/00 | (2006.01) |
| C12N 15/81 | (2006.01) |
| A61K 38/00 | (2006.01) |

(52) U.S. Cl.
CPC ................ *C07K 14/78* (2013.01); *A61K 8/64* (2013.01); *A61K 9/0014* (2013.01); *A61K 38/39* (2013.01); *A61K 38/46* (2013.01); *A61Q 19/00* (2013.01); *C07K 14/39* (2013.01); *C12N 9/00* (2013.01); *C12N 15/815* (2013.01); *A61K 38/00* (2013.01); *A61K 2800/85* (2013.01); *C07K 2319/00* (2013.01)

(58) Field of Classification Search
CPC ........ A61K 8/64; A61K 9/0014; A61K 38/39; A61K 38/46; A61K 2800/74; A61K 2800/85; C07K 14/78; C07K 2319/00
See application file for complete search history.

(56) References Cited

FOREIGN PATENT DOCUMENTS

| | | |
|---|---|---|
| CN | 105504066 A | 4/2016 |
| CN | 108794639 A | 11/2018 |
| CN | 110204608 B | 3/2020 |
| WO | 1990/008833 A1 | 8/1990 |

OTHER PUBLICATIONS

Li, Mingcai et al., "The Purification and Expression of Triple-domain Recombinant Fibronectin Polypeptide in *E. coli*," Acta Universitatis Medicinae Tongji, vol. 28, No. 5, pp. 381-384, Oct. 31, 1990.

*Primary Examiner* — Jeffrey E. Russel
(74) *Attorney, Agent, or Firm* — RABIN & BERDO, P.C.

(57) ABSTRACT

The invention discloses a yeast-fermented recombinant fibronectin peptide in small molecule, comprising at least one β subunit binding domain of sodium-potassium ATPase, wherein the amino acid sequence of the β subunit binding domain of sodium-potassium ATPase is shown in SEQ ID NO: 2. The invention also discloses a preparation method for the yeast-fermented recombinant fibronectin peptide in small molecule and applications of the yeast-fermented recombinant fibronectin peptide in small molecule. The yeast-fermented recombinant fibronectin peptide in small molecule of the present invention can be effectively absorbed by a skin, and has excellent healing and repairing effects on traumatic skin lesions or subcutaneous lesions with intact keratin.

8 Claims, 4 Drawing Sheets
Specification includes a Sequence Listing.

SEQUENCE LISTING

<160> NUMBER OF SEQ ID NOS: 7

<210> SEQ ID NO 1
<211> LENGTH: 371
<212> TYPE: PRT
<213> ORGANISM: Artificial Sequence
<220> FEATURE:
<223> OTHER INFORMATION: Synthetic peptide (yeast-fermented recombinant
      fibronectin peptide)

<400> SEQUENCE: 1

Ala Cys Ser Pro Pro His Ser Lys Ser His Cys Gly Gly Gly Gly Ser
1               5                   10                  15

Ile Gln Trp Asn Ala Pro Gln Pro Ser His Ile Ser Lys Tyr Ile Leu
            20                  25                  30

Arg Trp Arg Pro Lys Asn Ser Val Gly Arg Trp Lys Glu Ala Thr Ile
        35                  40                  45

Pro Gly His Leu Asn Ser Tyr Thr Ile Lys Gly Leu Lys Pro Gly Val
    50                  55                  60

Val Tyr Glu Gly Gln Leu Ile Ser Ile Gln Gln Tyr Gly His Gln Glu
65              70                  75                  80

Val Thr Arg Phe Asp Phe Thr Thr Thr Ser Thr Ser Thr Gly Gly Ser
            85                  90                  95

Ala Val Pro Pro Pro Thr Asp Leu Arg Phe Thr Asn Ile Gly Pro Asp
            100                 105                 110

Thr Met Arg Val Thr Trp Ala Pro Pro Pro Ser Ile Asp Leu Thr Asn
            115                 120                 125

Phe Leu Val Arg Tyr Ser Pro Val Lys Asn Glu Glu Asp Val Ala Glu
    130                 135                 140

Leu Ser Ile Ser Pro Ser Asp Asn Ala Val Val Leu Thr Asn Leu Leu
145                 150                 155                 160

Pro Gly Thr Glu Tyr Val Val Ser Val Ser Ser Val Tyr Glu Gln His
            165                 170                 175

Glu Ser Thr Pro Leu Arg Gly Arg Gln Lys Thr Gly Leu Asp Ser Pro
            180                 185                 190

Thr Gly Ile Asp Phe Ser Asp Ile Thr Ala Asn Ser Phe Thr Val His
        195                 200                 205

Trp Ile Ala Pro Arg Ala Thr Ile Thr Gly Tyr Arg Ile Arg His His
    210                 215                 220

Pro Glu His Phe Ser Gly Arg Pro Arg Glu Asp Arg Val Pro His Ser
225                 230                 235                 240

Arg Asn Ser Ile Thr Leu Thr Asn Leu Thr Pro Gly Thr Glu Tyr Val
            245                 250                 255

Val Ser Ile Val Ala Leu Asn Gly Arg Glu Glu Ser Pro Leu Leu Ile
            260                 265                 270

Gly Gln Gln Ser Thr Val Ser Asp Val Pro Arg Asp Leu Glu Val Val
        275                 280                 285

Ala Ala Thr Pro Thr Ser Leu Leu Ile Ser Trp Asp Ala Pro Ala Val
    290                 295                 300

Thr Val Arg Tyr Tyr Arg Ile Thr Tyr Gly Glu Thr Gly Gly Asn Ser
305                 310                 315                 320

Pro Val Gln Glu Phe Thr Val Pro Gly Ser Lys Ser Thr Ala Thr Ile
            325                 330                 335

Ser Gly Leu Lys Pro Gly Val Asp Tyr Thr Ile Thr Val Tyr Ala Val
            340                 345                 350

Thr Gly Arg Gly Asp Ser Pro Ala Ser Ser Lys Pro Ile Ser Ile Asn
        355                 360                 365

Tyr Arg Thr
    370

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide (beta subunit binding domain
      of sodium-potassium-ATPase)

<400> SEQUENCE: 2

Ala Cys Ser Pro Pro His Ser Lys Ser His Cys Gly Gly Gly Gly Ser
1               5                   10                  15

<210> SEQ ID NO 3
<211> LENGTH: 77
<212> TYPE: PRT
<213> ORGANISM: Artificial Sequence
<220> FEATURE:
<223> OTHER INFORMATION: Synthetic peptide (fibrin binding domain)

<400> SEQUENCE: 3

Ile Gln Trp Asn Ala Pro Gln Pro Ser His Ile Ser Lys Tyr Ile Leu
1               5                   10                  15

Arg Trp Arg Pro Lys Asn Ser Val Gly Arg Trp Lys Glu Ala Thr Ile
                20                  25                  30

Pro Gly His Leu Asn Ser Tyr Thr Ile Lys Gly Leu Lys Pro Gly Val
            35                  40                  45

Val Tyr Glu Gly Gln Leu Ile Ser Ile Gln Tyr Gly His Gln Glu
        50                  55                  60

Val Thr Arg Phe Asp Phe Thr Thr Thr Ser Thr Ser Thr
65                  70                  75

<210> SEQ ID NO 4
<211> LENGTH: 94
<212> TYPE: PRT
<213> ORGANISM: Artificial Sequence
<220> FEATURE:
<223> OTHER INFORMATION: Synthetic peptide (collagen binding domain)

<400> SEQUENCE: 4

Gly Gly Ser Ala Val Pro Pro Thr Asp Leu Arg Phe Thr Asn Ile
1               5                   10                  15

Gly Pro Asp Thr Met Arg Val Thr Trp Ala Pro Pro Ser Ile Asp
                20                  25                  30

Leu Thr Asn Phe Leu Val Arg Tyr Ser Pro Val Lys Asn Glu Glu Asp
            35                  40                  45

Val Ala Glu Leu Ser Ile Ser Pro Ser Asp Asn Ala Val Val Leu Thr
        50                  55                  60

Asn Leu Leu Pro Gly Thr Glu Tyr Val Val Ser Val Ser Ser Val Tyr
65                  70                  75                  80

Glu Gln His Glu Ser Thr Pro Leu Arg Gly Arg Gln Lys Thr
                85                  90

<210> SEQ ID NO 5
<211> LENGTH: 90
<212> TYPE: PRT
<213> ORGANISM: Artificial Sequence
<220> FEATURE:

<223> OTHER INFORMATION: Synthetic petide (domain of heparin)

<400> SEQUENCE: 5

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr
            85                  90

<210> SEQ ID NO 6
<211> LENGTH: 94
<212> TYPE: PRT
<213> ORGANISM: Artificial Sequence
<220> FEATURE:
<223> OTHER INFORMATION: Synthetic peptide (domain of fibronectin)

<400> SEQUENCE: 6

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
            85                  90

<210> SEQ ID NO 7
<211> LENGTH: 1113
<212> TYPE: DNA
<213> ORGANISM: Artificial Sequence
<220> FEATURE:
<223> OTHER INFORMATION: Synethetic nucleotide (recombinant fibronectin)

<400> SEQUENCE: 7
gcttgttctc cgcctcattc taaatctcat tgcggtggtg gcggttccat ccagtggaac    60
gctccgcagc cgtctcatat ctctaagtac atcctgcgct ggcgtccgaa aaactctgtg   120
ggtcgttgga agaagctac catccctggt catctgaact cctacacgat taaaggtctg    180
aaaccgggcg ttgtttatga aggtcagctg atctctatcc agcagtacgg tcaccaagaa   240
gttactcgtt ttgacttcac taccacttct acttctaccg tggttctgc tgtaccgccg    300 ccaaccgacc tgcgttttac gaacatcggt ccggatacta tgcgtgttac ttgggcaccg   360
ccgccttcca ttgatctgac caactttctg gtacgttact ctccggtcaa aaatgaagag   420
gacgttgctg aactgtctat ttctccgtcc gacaacgcag ttgttctgac taacctgctg   480
ccaggtaccg aatatgtggt gtctgtgagc tctgtttatg aacagcacga agcaccccg    540 ctgcgtggtc gtcagaaaac cggcctggat tccccgaccg gtatcgattt ttctgatatc   600

```
accgcaaata gcttcaccgt acattggatc gcaccgcgtg caaccatcac cggttatcgc      660
atccgtcacc acccggagca cttttctggc cgccctcgtg aagatcgtgt tccacattct      720
cgtaattcta tcaccctgac caacctgact ccgggcactg aatacgtggt cagcatcgtg      780
gcactgaacg gtcgcgaaga atctccgctg ctgatcggtc aacagagcac tgtgagcgac      840
gttcctcgtg acctggaagt agttgctgca acgccgacct ccctgctgat ctcttgggac      900
gctccagctg ttaccgttcg ttactatcgt attacttacg gtgaaaccgg cggtaactct      960
ccggtgcagg aatttaccgt cccgggcagc aaatctaccg ccacgatttc cggtctgaag     1020
ccgggcgttg attatactat caccgtttac gctgttaccg gtcgtggtga ctcccctgct     1080
tcctctaaac cgatctctat caactaccgt acg                                  1113
```

YEAST-FERMENTED RECOMBINANT FIBRONECTIN PEPTIDE IN SMALL MOLECULE, AND ITS PREPARATION METHOD AND APPLICATIONS THEREOF

Technical Field

The invention belongs to the field of bioengineering, and specifically relates to a yeast-fermented recombinant fibronectin peptide in small-molecule, and its preparation method and applications thereof.

BACKGROUND OF THE INVENTION

Fibronectin (FN) is a macromolecular glycoprotein with a sugar content of 4.5%-9.5% and a molecular weight of about 450 kd. It is widely present in plasma, a variety of cell surfaces and cell matrix. As an important adhesion molecule, it can bind to 11 kinds of integrin receptors and plays an extremely important function in the interaction between cells and between cells and matrix. A large number of studies have found that fibronectin (FN) is involved in wound healing, tissue repair, embryonic differentiation, immune response, tumor differentiation and metastasis, childbirth and other processes, and is closely related to many diseases. Fibronectin matrix polymerization also promotes type I collagen deposition and strengthens the structure of collagen-based tissue.

Fibronectin is a protein dimer, consisting of two nearly identical monomers linked by a pair of C-terminal disulfide bonds. The molecular weight of each fibronectin subunit is 230-250kDa, and they are composed of three repeating modules (modular structures), including: 12 Fibronectin type I repeats (FnI), 2 Fibronectin type II repeats (FnII), 15-17 repeats for Fibronectin type III (FnIII), 2 alternatively spliced repeats (EIIIA and EIIIB) and 1 Variable region (V). The above various modules constitute the functional domains of fibronectin, including: the N-terminal domain (FnI1-9) weight 70kDa; the 120-kDa central binding domain (CBD; FnIII1-12), and heparin-binding domain (HepII; FnIII12-14). Two FnIII produce ED (extradomain) A and B through alternative splicing (plasma fibronectin does not have EDA and EDB, but cellular fibronectin contains variable amounts of EDA or EDB). The vast majority of cellular fibronectins contain variable region V. Fibronectin recognizes and binds to integrin heterodimers through the arginine-glycine-aspartic acid sequence (Arg-Gly-Asp, RGD) on FnIII10, thereby affecting cell adhesion and migration. Fibronectin molecules also have other adhesion sites, which respectively bind to collagen, fibrin, heparin, etc., which together determine the stability of the extracellular matrix (ECM).

Fibronectin has a wide range of applications in the fields of medical treatment, beauty and scientific research, but the natural fibronectin extracted from human or animal blood and tissues is extremely limited in production and expensive in cost. In addition, the fibronectin molecule is too large (contains more than 2000 amino acids and weight of about 45 kDa), which is difficult to be absorbed by skin with complete keratinous structure. Therefore, the market application of FN is limited, especially in the field of beauty and skin care.

SUMMARY OF THE INVENTION

In order to solve the above problems, the present invention is based on the yeast system to obtain the active structure of recombinant fibronectin. Therefore, the first purpose of the present invention is to provide a recombinant fibronectin peptide in small-molecule fermented by yeast to solve the problems of low yield and low stability obtained by the existing E. coli expression system. The second purpose of the present invention is to provide the expression vector Chimeric FN. The third purpose of the present invention is to provide a method for preparing recombinant fibronectin peptides in small-molecule fermented by yeast. The fourth purpose of the present invention is to provide applications of yeast-fermented recombinant fibronectin peptide in small molecule.

In order to achieve the above purposes, the present invention adopts the following technical solutions:

As the first aspect of the present invention, a yeast-fermented recombinant fibronectin peptide in small molecule includes following amino acid sequence: (β-subunit binding domain of sodium-potassium-ATPase, and the amino acid sequence of the (β-subunit binding domain of sodium-potassium-ATPase is shown in SEQ ID NO: 2.

According to the present invention, the yeast-fermented recombinant fibronectin peptide in small-molecule further includes the following amino acid sequence:

a fibrin binding domain, wherein the amino acid sequence of the fibrin binding domain is as shown in SEQ ID NO: 3;

a collagen binding domain, wherein the amino acid sequence of the collagen binding domain is shown in SEQ ID NO: 4;

a domain of heparin, wherein the amino acid sequence of the domain of heparin is shown in SEQ ID NO: 5;

a domain of fibronectin, which includes the integrin binding domain of fibronectin as shown in SEQ ID NO:6.

Furthermore, the yeast-fermented recombinant fibronectin peptide in small-molecule includes amino acid sequence shown in SEQ ID NO: 1, and the amino acid sequence shown in SEQ ID NO: 1 is connected by amino acid sequence shown in SEQ ID NO: 2, SEQ ID NO: 3, SEQ ID NO: 4, SEQ ID NO: 5 and SEQ ID NO: 6 in sequence.

As the second aspect of the present invention, there is a nucleotide sequence encoding the aforementioned yeast-fermented recombinant fibronectin peptide in small molecule, and the nucleotide sequence is as set forth in SEQ ID NO: 7.

As the third aspect of the present invention, an expression vector Chimeric FN includes the amino acid sequence shown in SEQ ID NO:1.

Furthermore, the expression vector Chimeric FN includes the nucleotide sequence as shown in SEQ ID NO: 7, which is inserted into pPIC9K vector.

As the fourth aspect of the present invention, a method for preparing a recombinant fibronectin peptide in small-molecule fermented by yeast includes the following steps:

(a). inserting a nucleotide sequence shown in SEQ ID NO: 7 into a pPIC9K vector to obtain an expression plasmid encoding Chimeric FN protein;

(b). extracting and linearizing genomic DNA of the expression plasmid encoding Chimeric FN protein of (a), then mixing it with competent Pichia pastoris, transferring it to an electroporation cuvette and placing the cuvette on ice; then adding pre-chilled sorbitol, spreading stuffs on MD plates, incubating them until clones are produced, and screening Mut+/Muts strains which can express recombinant fibronectin;

(c): performing expression and purification of the Mut+/Muts strains screened in (b).

As the fifth aspect of the present invention, a yeast-fermented recombinant fibronectin peptide in small molecule is used to promote cell adhesion and growth.

As the sixth aspect of the present invention, a yeast-fermented recombinant fibronectin peptide in small molecule is used in preparation of a medicine for treating skin injury, healing and repairing.

As the seventh aspect of the present invention, a pharmaceutical composition includes the aforementioned yeast-fermented recombinant fibronectin peptide in small molecule.

As the eighth aspect of the present invention, a cosmetic composition includes the above-mentioned yeast-fermented recombinant fibronectin peptide in small molecule.

The beneficial effects of the present invention: the present invention uses Pichia pastoris as a host to express glycosylated fibronectin, which has good heat resistance, high glycosylation degree, high yield, strong activity, can be effectively absorbed by the skin, and have excellent healing and repairing effects on trauma type skin lesions or subcutaneous injuries with intact cuticle. The recombinant fibronectin obtained by the present invention can be used clinically for skin damage repair, and can be used for sensitive skin repair in the field of cosmetics.

DETAILED DESCRIPTION

The present invention will be further described below in conjunction with specific examples. It should be understood that the following examples are only used to illustrate the present invention and not to limit the scope of the present invention.

Embodiment 1 Construction of an expression plasmid encoding Chimeric FN

Figure 1:
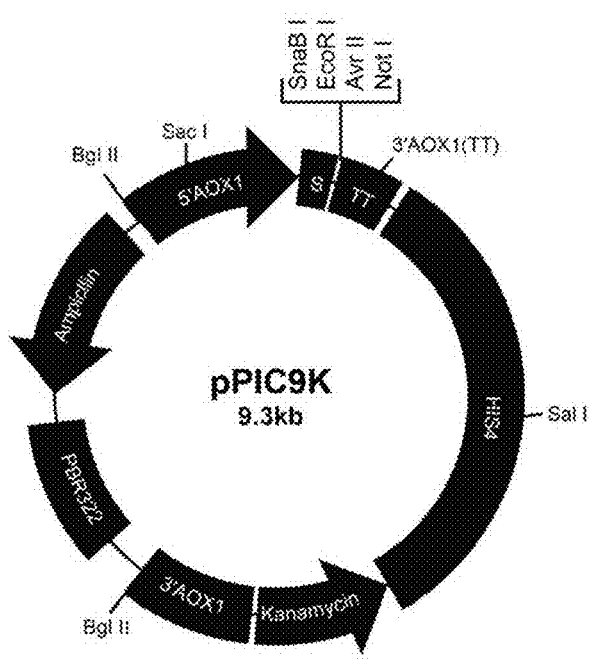
FIG. 1 shows the sequence map of pPIC9k vector.
Figure 2:
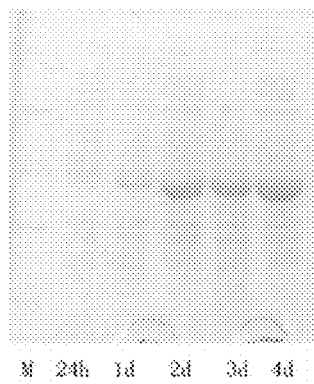
FIG. 2 shows the fermentative expression of recombinant fibronectin.

This embodiment uses the commercial vector pPIC9K (shown in FIG. 1), purchased from Proteintech Group, Inc in Wuhan. Design and Select the restriction sites EcoR I and Not I according to the relevant sequence tagged sites in FIG. 1. The gene sequences encoding Chimeric FN is made up of artificially optimized codons preferred by Pichia pastoris, which is obtained by artificial synthesis. The full-length DNA fragment of the synthesized recombinant fibronectin has a restriction endonuclease at both 5' end and 3' end, corresponding to EcoR I and Not I, respectively. The target fragment of recombinant fibronectin will be inserted between these two restriction sites to obtain an expression plasmid encoding Chimeric FN protein. Among them, the amino acid sequence of recombinant fibronectin is:

(SEQ ID NO: 1)
ACSPPHSKSHCGGGGSIQWNAPQPSHISKYILRWRPKNSVGRWKEATIPG

HLNSYTIKGLKPGVVYEGQLISIQQYGHQEVTRFDFTTTSTSTGGSAVPP

PTDLRFTNIGPDTMRVTWAPPPSIDLTNFLVRYSPVKNEEDVAELSISPS

DNAVVLTNLLPGTEYVVSVSSVYEQHESTPLRGRQKTGLDSPTGIDFSDI

TANSFTVHWIAPRATITGYRIRHHPEHFSGRPREDRVPHSRNSITLTNLT

PGTEYVVSIVALNGREESPLLIGQQSTVSDVPRDLEVVAATPTSLLISWD

APAVTVRYYRITYGETGGNSPVQEFTVPGSKSTATISGLKPGVDYTITVY

AVTGRGDSPASSKPISINYRT

The fibronectin specifically includes the following amino acid sequence: (1) at least one (β-subunit binding domain of sodium-potassium-ATPase, the amino acid sequence of the (β-subunit binding domain of sodium-potassium-ATPase is shown in SEQ ID NO: 2; (2) At least one fibrin binding domain, the amino acid sequence of the fibrin binding domain is shown in SEQ ID NO: 3; (3) at least one collagen binding domain, the amino acid sequence of the collagen binding domain is shown in SEQ ID NO: 4; (4) At least one domain of heparin, whose amino acid sequence is shown in SEQ ID NO: 5; (5) The structure of at least one fibronectin domain, the domain of fibronectin at least includes the integrin binding domain of fibronectin as shown in SEQ ID NO:6.

(SEQ ID NO: 2)
ACSPPHSKSHCGGGGS (SEQ ID NO: 3)
IQWNAPQPSHISKYILRWRPKNSVGRWKEATIPGHLNSYTIKGLKPGVVY

EGQLISIQQYGHQEVTRFDFTTTSTST (SEQ ID NO: 4)
GGSAVPPPTDLRFTNIGPDTMRVTWAPPPSIDLTNFLVRYSPVKNEEDVA

ELSISPSDNAVVLTNLLPGTEYVVSVSSVYEQHESTPLRGRQKT (SEQ ID NO: 5)
GLDSPTGIDFSDITANSFTVHWIAPRATITGYRIRHHPEHFSGRPREDRV

PHSRNSITLTNLTPGTEYVVSIVALNGREESPLLIGQQST (SEQ ID NO: 6)
VSDVPRDLEVVAATPTSLLISWDAPAVTVRYYRITYGETGGNSPVQEFTV

PGSKSTATISGLKPGVDYTITVYAVTGRGDSPASSKPISINYRT

The nucleotide sequence of recombinant fibronectin is:

(SEQ ID NO: 7)
1 GCTTGTTCTC CGCCTCATTC TAAATCTCAT TGCGGTGGTG

GCGGTTCCAT CCAGTGGAAC GCTCCGCAGC

-continued

```
 71 CGTCTCATAT CTCTAAGTAC ATCCTGCGCT GGCGTCCGAA

AAACTCTGTG GGTCGTTGGA AAGAAGCTAC

141 CATCCCTGGT CATCTGAACT CCTACACGAT TAAAGGTCTG

AAACCGGGCG TTGTTTATGA AGGTCAGCTG

211 ATCTCTATCC AGCAGTACGG TCACCAAGAA GTTACTCGTT

TTGACTTCAC TACCACTTCT ACTTCTACCG

281 GTGGTTCTGC TGTACCGCCG CCAACCGACC TGCGTTTTAC

GAACATCGGT CCGGATACTA TGCGTGTTAC

351 TTGGGCACCG CCGCCTTCCA TTGATCTGAC CAACTTTCTG

GTACGTTACT CTCCGGTCAA AAATGAAGAG

421 GACGTTGCTG AACTGTCTAT TTCTCCGTCC GACAACGCAG

TTGTTCTGAC TAACCTGCTG CCAGGTACCG

491 AATATGTGGT GTCTGTGAGC TCTGTTTATG AACAGCACGA

AAGCACCCCG CTGCGTGGTC GTCAGAAAAC

561 CGGCCTGGAT TCCCCGACCG GTATCGATTT TTCTGATATC

ACCGCAAATA GCTTCACCGT ACATTGGATC

631 GCACCGCGTG CAACCATCAC CGGTTATCGC ATCCGTCACC

ACCCGGAGCA CTTTTCTGGC CGCCCTCGTG

701 AAGATCGTGT TCCACATTCT CGTAATTCTA TCACCCTGAC

CAACCTGACT CCGGGCACTG AATACGTGGT

771 CAGCATCGTG GCACTGAACG GTCGCGAAGA ATCTCCGCTG

CTGATCGGTC AACAGAGCAC TGTGAGCGAC

841 GTTCCTCGTG ACCTGGAAGT AGTTGCTGCA ACGCCGACCT

CCCTGCTGAT CTCTTGGGAC GCTCCAGCTG

911 TTACCGTTCG TTACTATCGT ATTACTTACG GTGAAACCGG

CGGTAACTCT CCGGTGCAGG AATTTACCGT

981 CCCGGGCAGC AAATCTACCG CCACGATTTC CGGTCTGAAG

CCGGGCGTTG ATTATACTAT CACCGTTTAC

1051 GCTGTTACCG GTCGTGGTGA CTCCCCTGCT TCCTCTAAAC

CGATCTCTAT CAACTACCGT ACG
```

The recombinant DNA fragment was entrusted to NovoPro Bioscience Inc. in Shanghai to synthesize; the expression plasmid encoding Chimeric FN protein was entrusted to NovoPro Bioscience Inc. in Shanghai to construct.

Embodiment 2 The expression, purification and electrophoresis method of recombinant fibronectin for identification 1) Preparation of yeast clones. Extract the genomic DNA of the expression vector Chimeric FN, cut with nuclease to obtain linearized DNA, and dissolve the linearized DNA in 5-10 µl TE (purchased from NovoPro). Take 80 µl of commercial competent Pichia pastoris GS115 (purchased from Tiangen Biotech), mix with 10 µg of linearized DNA, and transfer to a pre-cooled 0.2 cm electroporation cuvette. Place on ice for 5 minutes. Set the machine parameters, immediately add 1 ml of pre-chilled 1M sorbitol to the cuvette, transfer the contents to a sterile centrifuge tube and divide them into 200 µl aliquots, spread them on the MD plate, incubate the plate at 30 ° C. until clones are generated. Due to the transformed vector contains the Mut gene, and only the successfully transformed strains can be screened by the mut phenotype, the Mut+/Muts strains can be preserved through screening.

2) Expression and purification of recombinant fibronectin. Pick a single clone, inoculate it into 25ml BMGY medium (Buffered Glycerol-complex Medium), in 250 ml shake flask, at 30° C. and 250rpm until the OD600 is 4, then centrifuge at 3000g at room temperature for 5min, collect the cells, decant the supernatant, and use BMMY medium to resuspend the cells pellets to OD600 of 1.0 for expression of induction. Add the above-mentioned culture to a 1 L shake flask, cover the flask with two layers of sterilized gauze or cheesecloth, and put it in a shaker to continue to grow. Every 24 hours, add methanol to a final concentration of 0.5% to continue induction. At multiple time points, take 1 ml of medium into a 1.5 mL centrifuge tube. These samples are used to analyze expression levels and determine the optimal time to collect cells after induction. Centrifuge in a horizontal centrifuge at maximum speed for 2-3 minutes at room temperature. For secretory expression, transfer the supernatant into a separate tube, and store the supernatant and cell pellet at -80 degrees until the test starts. Use Coomassie Brilliant Blue staining for SDS-PAGE, western blotting or functional analysis method to analyze the protein expression of supernatant and cell pellet (SDS-PAGEp47).

After testing, the expression level of yeast clone of recombinant fibronectin changed with time. After 4 days of induction, the protein yield reached 2 g/L as shown in picture 2.

Conclusion: Using the Pichia pastoris expression system, high-yield recombinant fibronectin in small-molecule fermented by yeast can be obtained. 3) Centrifuge the bacteria fermented liquid at 3000 g for 5 minutes, collect the supernatant, and discard the precipitate. Let the protein in the supernatant bind to the Phenyl column, and elute with 20 mM phosphate buffer at pH7.5 after the binding is complete. The eluted protein is bound to the anion exchange resin, and then eluted with 150 mM NaCl, 20 mM phosphate 0.5 M urea solution. The purity of the obtained protein was identified by SDS-PAGE electrophoresis, and the protein band was single, without degradation band, and the purity was greater than 95%.

4) Setting of the control group: Replace the Pichia pastoris in the step of preparation of yeast clone with Escherichia coli BL21, the other steps and conditions are the same, and the amino acid sequence of fibronectin is also shown in SEQ ID NO:1. Recombinant fibronectin expressed in E. coli host is obtained.

As a result, the expression level of fibronectin expressed by the E. coli system was similar to the expression level of fibronectin expressed by the yeast system.

Figure 3:
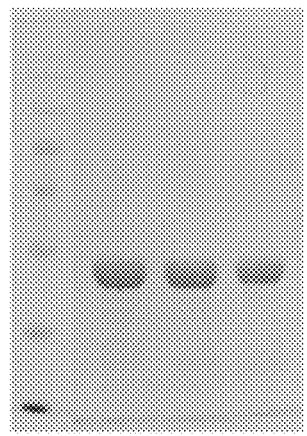
FIG. 3 shows the expression level of the purified recombinant fibronectin, which reflects three positions of the same elution peak.
Figure 4:
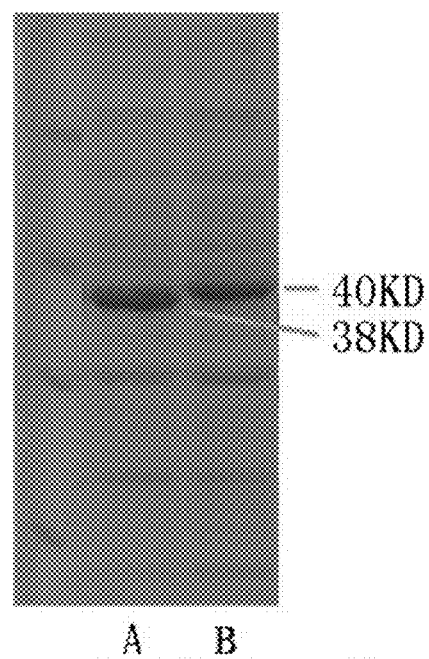
FIG. 4 shows the protein molecular weight of recombinant fibronectin. Among them, A is fermented by E. coli without glycosylation; B is fermented by Pichia pastoris, containing glycosylation.

However, the recombinant fibronectin expressed in the E. coli host is not glycosylated; the molecular weight of FN expressed in yeast is higher than expected. This is because the recombinant fibronectin expressed by yeast contains glycosylation modification, and glycosylation is an important part of maintaining the activity of fibronectin. Please refer to FIG. 3 and FIG. 4 for the results.

Conclusion: The recombinant fibronectin expressed by Pichia pastoris is glycosylated, and the expressed fibronectin is closer to the natural state.

Embodiment 3 Recombinant fibronectin was tested for promoting cell adhesion and growth The recombinant fibronectin purified in Embodiment 2 was formulated into multiple concentrations (1, 6, 9, 15, 24

µg/ml), then coated in a 96-well plate for 30 minutes, and washed twice with PBS. Add 1% BSA and block at 37° C. for 30 minutes, then add rat fibroblasts (cultured in serum-free medium), 1 h later, gently aspirate the medium in the wells, gently rinse the unadsorbed cells with PBS, and use CCD8 method to detect the number of live cells adsorbed on the bottom of the well plate to verify the activity of recombinant fibronectin. Please refer to FIG. 5 and FIG. 6 for the results.

Figure 5:
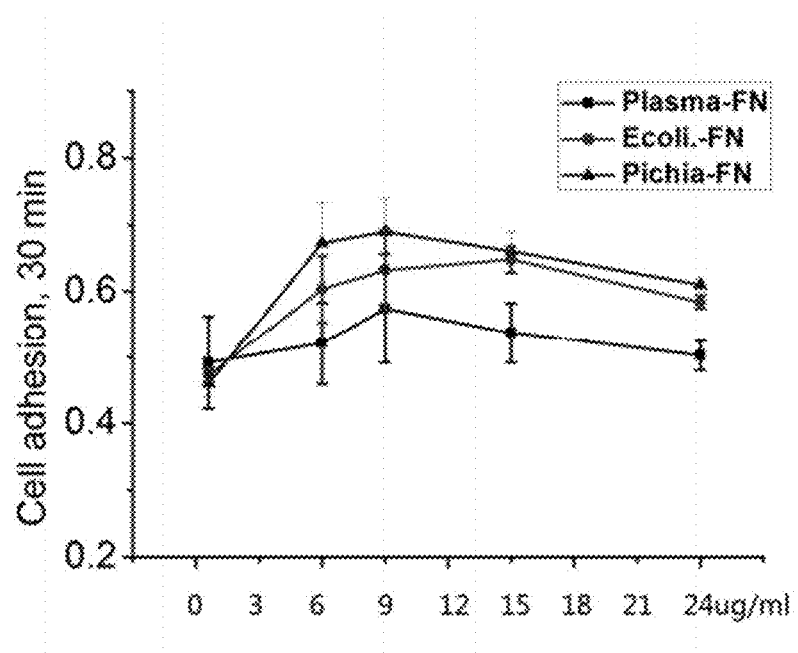
FIG. 5 is a graph showing the results of recombinant fibronectin promoting cell adhesion.

The results of FIG. 5 show that the cell-adhesive activity of recombinant fibronectin is better than fibronectin in natural structure. Yeast-fermented protein has a significantly greater effect on cell adhesion than E. coli fermented protein, because glycosylation plays an important role in cell adhesion.

Figure 6:
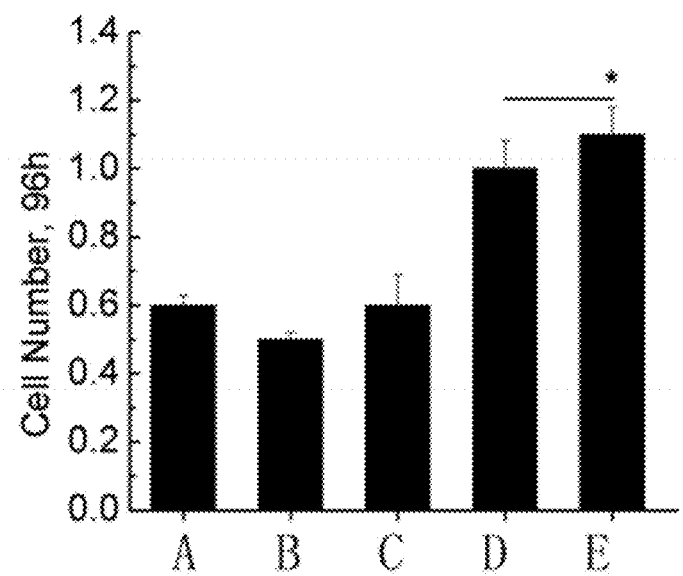
FIG. 6 is a graph showing the results of the effect of recombinant fibronectin on promoting cell growth. Among them, A is collagen; B is gelatin; C is plasma fibronectin; D is fibronectin expressed in E. coli; E is fibronectin expressed in Pichia pastoris.

The results of FIG. 6 show the effects of various cell adhesion on cell growth. Group A is collagen purchased from Sangon Biotech (Shanghai) Co., Ltd., Group B is gelatin purchased from Sangon Biotech (Shanghai) Co., Ltd., and Group C is plasma fibronectin purchased from Thermofisher, which is extracted and purified from human plasma, representing fibronectin of natural origin, group D is fibronectin expressed in E. coli (consistent with the control group in Embodiment 2), group E is the recombinant fibronectin expressed in Pichia pastoris, obtained through Embodiment 2. It can be seen from FIG. 6 that the recombinant fibronectin obtained in the present invention has excellent activity of promoting cell growth, and its effect is significantly different from that expressed in E. coli, and is better than plasma fibronectin and other conventional cell adhesives.

Embodiment 4 Stability detection of recombinant fibronectin

Prepare three equal concentrations of 500 µg/ml serum-derived fibronectin (Plasma-FN) solution (extracted and purified from human plasma, representing natural fibronectin, without binding domain of Na+/K+-ATPase), fibronectin fermented by E. coli (Ecoli.-FN) (consistent with the control group in Embodiment 2, representing non-glycosylated fibronectin) and yeast-derived fibronectin (Pichia-FN, the purified recombinant fibronectin in Embodiment 2) (solvent: 20mM PBS, pH7.5) and stored them in a sealed 10 ml penicillin bottle, and placed in different temperature environments. And observe the clarity of the solution at different times. Determine quantitative of protein concentration by BCA method. The two temperatures of accelerated testing set in this embodiment are 37° C. and 55° C., respectively, to observe the stability of the protein in an environment of 37° C. and the time to reach a stable concentration in an environment of 55° C. The sampling time for detection of the 37° C. experiment set in this embodiment is: 1 h, 3 h, 6 h, 12 h, 24 h, and the sampling time for detection of the 55° C. experiment is: 1 h, 3 h, 7 h, 15 h, 30 h, 60 h. The results are shown in FIG. 7 and FIG. 8.

Figure 7:
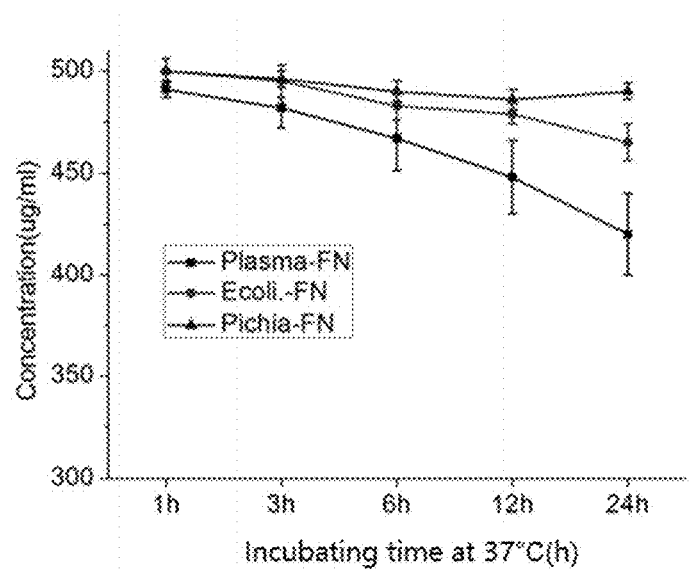
FIG. 7 shows the results of the stability of the sample under test at 37° C.

The results of FIG. 7 show that, in an environment of 37° C., within 24 hours, the concentration of yeast-derived protein did not significantly decrease, while the content of fibronectin fermented by E. coli and serum-derived was significantly reduced, the fibronectin aggregated to varying degrees and the fluid appears translucent and turbid.

Figure 8:
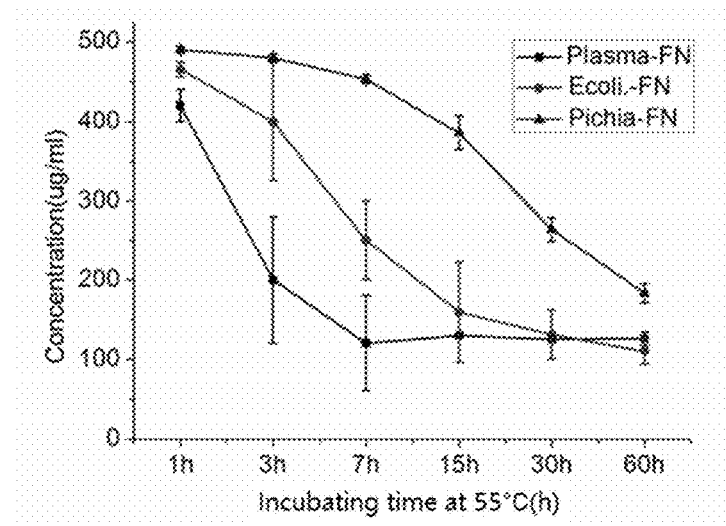
FIG. 8 shows the results of the stability of the sample under test at 55° C.

The results in FIG. 8 show that most proteins will usually get loss to aggregate, precipitate or degrade at a high temperature of 55° C.

Conclusion: Pichia-FN has good heat resistance and can be stable for 10 hours at 55° C. Plasma-FN and Ecoli.-FN began to accumulate and precipitate in a high temperature environment for about 3 hours. Among them, the loss rate of Plasma-FN reached 70%.

Embodiment 5 Skin penetration efficiency of purified fibronectin in Embodiment

Figure 9:
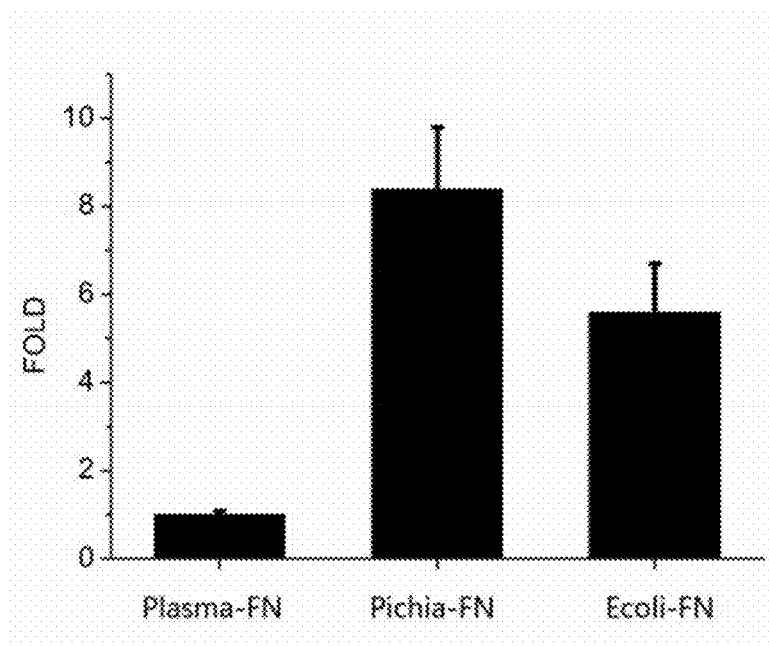
FIG. 9 shows the transdermal absorption of Pichia-FN, Plasma-FN and Ecoli-FN.

Put the depilated SD rats on their backs and fix them on the experimental table, insert the blood collection needle into the heart of the rat, collect blood with a vacuum blood collection tube, and drain the blood of the rat. After waiting for a period of time to confirm that the rat is dead, use a scalpel blade to make a crack along the edge of the exposed skin, and use surgical tweezers to clamp the skin to peel off the skin. Soak the peeled skin in PBS to rinse, and check the subcutaneous tissue residue. If there are too many subcutaneous tissue residues, trim the subcutaneous tissue with ophthalmic scissors to remove the subcutaneous tissue. Install the peeled skin tissue into the Franz transdermal diffusion cell, and fix the drug delivery slot and drug receiving slot. Add the drug receiving solution (PBS) to the drug receiving tank to remove air bubbles and check the tightness of the device. Put the diffusion tank, which is mounted with skin, into the water bath, and set the stirring speed of rotor to 300 rpm and the water bath temperature to 32° C. After adding 500 µL, of the appropriate concentration of recombinant protein to the drug delivery tank, and perform transdermal administration, 100 µL, of sample is collected from the receiving tank and used for quantitative addition with the fibronectin-linked immunoassay kit. Then calculated the value of Pichia-FN/Plasma-FN and Ecoli-FN/Plasma-FN, the detection kit was purchased from Boster Biological Technology co.ltd. The result is shown in FIG. 9.

The results show that the content of recombinant fibronectin through the skin is significantly higher than that of natural fibronectin in the serum. The transdermal absorption of Ecoli-FN is about 5 times that of Plasma-FN; while the absorption of Pichia-FN is about 8 times that of Plasma-FN.

Conclusion: The transdermal amount of Pichia-FN is significantly higher than that of Ecoli-FN, which is due to the β subunit binding domain of Na+/K+-ATPase is protected by glycosyl groups, which activity is fully protected. The binding domain and the β subunit of Na+K+ATPase can bind to each other to change the cutaneous intercellular space, The efficiency of molecule penetration through the intercellular space is further improved.

In summary, the recombinant fibronectin of the present invention has better skin absorption function, and can be better applied to the field of beauty and skin care through the epidermal layer with complete keratin structure.

The basic principles, main features and advantages of the present invention have been shown and described above. Technical personnel in this industry should understand that the present invention is not limited by the above-mentioned embodiments. The above-mentioned embodiments and the description only illustrate the principles of the present invention. The present invention will have various aspects without departing from the spirit and scope of the present invention. Various changes and improvements, these changes and improvements all should fall within the scope of the claimed invention. The scope of protection claimed by the present invention is defined by the appended claims and their equivalents. For example, the sequence of the embodiment of the present invention is only used to explain the present invention, and those technical personnel can redesign primers and probes to detect other target gene sequences according to the principles of the present invention.

The invention claimed is:

1. A recombinant fibronectin peptide, comprising sequentially-connected amino acid sequences of:
a β subunit binding domain of sodium-potassium-ATPase, wherein the amino acid sequence of the β subunit binding domain of sodium-potassium-ATPase is shown in SEQ ID NO: 2;
a fibrin binding domain, wherein the amino acid sequence of the fibrin binding domain is shown in SEQ ID NO: 3;
a collagen binding domain, wherein the amino acid sequence of the collagen binding domain is shown in SEQ ID NO: 4;
a heparin-binding domain, wherein the amino acid sequence of the heparin-binding domain is shown in SEQ ID NO: 5; and
a domain of fibronectin, wherein the domain of fibronectin includes an integrin binding domain of fibronectin as shown in SEQ ID NO: 6.

2. An isolated nucleotide as set forth in SEQ ID NO: 7.

3. An expression vector Chimeric Fibronectin including a nucleotide sequence encoding an amino acid sequence shown in SEQ ID NO:1.

4. A method for preparing a recombinant fibronectin peptide, comprising:
inserting a nucleotide sequence shown in SEQ ID NO: 7 into a pPIC9K vector to obtain an expression plasmid encoding Chimeric FN protein;
extracting and linearizing genomic DNA of the expression plasmid encoding Chimeric FN protein, then mixing with competent Pichia pastoris, screening Mut+/Muts strains which express recombinant fibronectin after clones are produced; and
performing expression and purification of the screened Mut+/Muts strains, thereby obtaining the recombinant fibronectin peptide.

5. A method of using the recombinant fibronectin peptide of claim 1, comprising using the recombinant fibronectin peptide in promoting both cell adhesion and cell growth.

6. A method of using the recombinant fibronectin peptide of claim 1, comprising using the recombinant fibronectin peptide in preparation of a medicine for treatment of skin injury, skin healing and skin repairing.

7. A pharmaceutical composition, comprising the recombinant fibronectin peptide of claim 1.

8. A cosmetic composition, comprising the recombinant fibronectin peptide of claim 1.

* * * * *